(12) United States Patent
Wilk (10) Patent No.: US 6,273,903 B1
(45) Date of Patent: Aug. 14, 2001

(54) ENDOSCOPIC STAPLING DEVICE AND RELATED STAPLE

(76) Inventor: Peter J. Wilk, 185 W. End Ave. - Unit 22M, New York, NY (US) 10023

( * ) Notice: Subject to any disclaimer, the term of this patent is extended or adjusted under 35 U.S.C. 154(b) by 0 days.

(21) Appl. No.: 09/435,148

(22) Filed: Nov. 8, 1999

(51) Int. Cl.[7] .................................................. A61B 17/08
(52) U.S. Cl. .......................... 606/219; 606/142; 606/151
(58) Field of Search .................................. 606/138–139, 606/142–143, 219, 151; 411/457

(56) References Cited

U.S. PATENT DOCUMENTS

| | | |
|---|---|---|
| 943,263 | 12/1909 | Moraweck . |
| 1,510,416 | 9/1924 | Pietz et al. . |
| 2,113,246 | 4/1938 | Wappler . |
| 2,968,041 | 1/1961 | Skold . |
| 3,378,010 | 4/1968 | Codling et al. . |
| 3,518,993 | 7/1970 | Blake . |
| 3,958,576 | 5/1976 | Komiya . |
| 4,038,987 | 8/1977 | Komiya . |
| 4,321,002 * | 3/1982 | Froehlich ............................. 411/457 |
| 4,367,746 | 1/1983 | Derechinsky . |
| 4,394,864 | 7/1983 | Sandhaus . |
| 4,485,817 | 12/1984 | Swiggett . |
| 4,681,107 | 7/1987 | Kees, Jr. . |
| 4,714,075 | 12/1987 | Krauter et al. . |
| 4,735,194 | 4/1988 | Stiegmann . |
| 4,759,364 | 7/1988 | Boebel . |
| 4,821,721 | 4/1989 | Chin et al. . |
| 4,880,015 | 11/1989 | Nierman . |
| 4,887,612 | 12/1989 | Esser et al. . |
| 4,945,920 | 8/1990 | Clossick . |
| 5,049,153 | 9/1991 | Nakao et al. . |
| 5,156,609 | 10/1992 | Nakao et al. . |
| 5,222,961 | 6/1993 | Nakao et al. . |
| 5,304,204 | 4/1994 | Bregen . |
| 5,833,695 * | 11/1998 | Yoon ..................................... 606/139 |

* cited by examiner

*Primary Examiner*—Cary E. O'Connor
(74) *Attorney, Agent, or Firm*—R. Neil Sudol; Henry D. Coleman; Coleman Sudol Sapone, P.C.

(57) ABSTRACT

A surgical staple, particularly but not exclusively for use in endoscopic surgery, includes a first leg, a second leg, and a hinge portion joining the first leg and the second leg to one another. A spring element is connected between the first leg and the second leg biases the staple in a closed postfiring configuration. The staple is temporarily disposed in an open prefiring configuration in an access tube by a stalk holding the legs of the staple apart. A stapling operation includes manipulating the stalk to affix the staple to a soft substrate, and subsequently withdrawing the stalk to release the staple and allow the spring element to develop closing force in the legs. The spring element may be integral with the legs or a separate element connected thereto.

24 Claims, 5 Drawing Sheets

ENDOSCOPIC STAPLING DEVICE AND RELATED STAPLE

FIELD OF THE INVENTION

This invention relates to a stapling device and to an associated surgical staple. More particularly, this invention relates to a device usable with an endoscope and/or in a laparoscopic surgical procedure for performing a stapling operation on a patient's internal body tissues at a surgical site not visible to the unaided eye.

BACKGROUND OF THE INVENTION

Stapling is known in the surgical arts as an alternative to suturing as a method of mechanically fastening cut or torn human tissue as an aid in the healing process. Stapling, or the use of independent rigid or semi-rigid multiple prong penetrating fasteners, enjoys several broad advantages relative to suturing. While suturing in effect results in a customized wound closure, stapling is faster and eliminates tasks requiring direct manipulation of tissue by a doctor or technician. The latter feature is paramount in cases where such manipulation is impractical or impossible, such as in endoscopy or laparoscopy or other minimally invasive surgical techniques. Such techniques characteristically require manipulation and repair of bodily tissues which cannot be directly seen or touched by a physician. Suturing has not proven practicable under these conditions using existing technology. Hence there is a continuing demand for improved methods of fastening for use in minimally invasive surgical techniques, and in particular, improved and various methods of stapling.

In minimally invasive surgery, operating space is at a premium, and in particular, dimensional extension in directions transverse to a longitudinal axis of a laparoscopic or endoscopic device is severely limited. Devices employed in the corresponding surgical tasks, such as endoscopes and laparoscopes generally have one elongate and two limited transverse dimensions: the resulting operational problem is analogous to constructing a model ship through the narrow neck of a bottle. Existing solutions to the problem of delivering a staple through a narrow channel in an endoscopic or laparoscipic procedure include fasteners or clamps which are biased closed, fed to an operating site in a closed configuration and forced open by a stapling tool at a point of use. Upon release by the tool, the fastener clamps intervening tissue. Another solution is to feed a fastener in a distorted closed configuration to the operating site, allow the fastener to open under internal spring forces just prior to application, and force the fastener closed a second time in an undistorted closed configuration, permitting engagement of locking elements to maintain the fastener in a closed configuration.

While endoscopic fastening devices certainly exist, the field is not mature, and a novel fastening assembly employing a parameter set or design choices not universally inferior in result to existing sets of parameters of design choices has a positive probability of proving superior to existing devices in solving some particular surgical problem. In particular, a novel surgical fastening device or assembly, allowing, relative to prior art, either a greater variety of fastener types to be inserted into a patient's body, or insertion at novel orientations relative to a distal tip of a minimally invasive surgical device, has a prima facie utility in the minimally invasive surgical arts.

OBJECTS OF THE INVENTION

An object of the present invention is to provide a surgical staple assembly for use in endoscopic surgical procedures to close openings internal to a patient's body.

Another object of the present invention is to provide an associated staple for use in endoscopic surgical procedures to close openings internal to a patient's body.

Yet a further object of the present invention is provide a surgical staple and related surgical staple assembly which substantially expands the functionality of existing endoscopic surgical staplers in at least one aspect.

These and other objects of the present invention will be apparent from the drawings and descriptions herein.

SUMMARY OF THE INVENTION

A surgical fastener in the form of a staple generally includes two legs which pierce and compress an intervening mass or body of tissue. A tensile force is thereby transferred to an intermediate portion of the staple, or bight, joining the two legs. The staple thereby serves as a bridge, temporarily assuming tensile force or stress which would have been assumed by cut or torn tissue, bring edges or lips of the cut together, in order to promote healing.

Force developed by a staple in compressing or resisting separating forces on intervening material is elastic in origin; i.e., developed by the staple in reaction to strain or deformation from an equilibrium configuration. The equilibrium configuration in turn may be modified in situ, following plastic deformation of a fastener having appropriate cold working properties by a fastening tool, or be preloaded in the form of a spring bias. The latter nomenclature calls attention to a design emphasis on strain in a particular element of a structure, a "spring element," while regarding a remainder of a structure as essentially rigid.

A staple body as a whole, comprising integral legs and optionally prongs or piercing elements, may be constructed from a material allowing substantial elastic deformation without plastic deformation, such as a spring steel, and thereby enjoy an elastic bias or equilibrium configuration from which substantial elastic deviations may be enjoyed. When an equilibrium configuration is fixed prior to use, and plastic deformation of a staple during a stapling operation is not contemplated, the staple or fastener may also conventionally be called a "clamp."

Yet another means of altering an equilibrium configuration of a fastener during use, as an alternative to plastic deformation, is the employment of locking elements. Locking elements in effect permit a change in overall equilibrium configuration by the introduction of permanent internal stresses. The distinction between "clamps," "staples" and other mechanical fasteners which may be envisaged for use in surgical procedures is blurred by invention.

The present invention is directed to a staple in the form of a clamp, or spring-loaded fastener, biased towards a closed use configuration, in which the fastener or staple grasps and compresses a mass of intervening tissue, thereby occluding or closing an intervening tear in the tissue. The invention is also directed to an associated stapler assembly, incorporating at least one staple in a tool adapted for insertion into a patient's body through a narrow channel, such as a biopsy channel of an endoscope or laparoscope, and a mechanism for placement and release of the staple from the staples assembly into the patient's tissue.

In particular, a stapler assembly in accordance with the present invention comprises at least one spring-loaded staple and a stalk, or elongate manipulating member, on which the staple is disposed in an open, prefiring configuration. The staple is spring-biased towards a closed or postfiring configuration. The staple in turn comprises two legs joined to one another and spring biased towards the closed configuration where the legs are adjacent and substantially parallel. The legs may be parts of a single body member having an elastic bight which functions in producing elastic bias, or clamping, forces. Alternatively, a separate spring element may be connected to the legs, which are coupled at a hinge joint. In either case, a pair of prongs or penetrating elements are located at free ends of the legs and are oriented so as to grasp a section of intervening soft tissue as the staple tends towards a closed configuration.

In accordance with another feature of the present invention, eyelets mounted on the legs, or apertures in the leg portions, enable the staple to be mounted on the stalk in a spread open configuration, the stiffness of the stalk being sufficient to maintain the legs in the open, prefiring, configuration, where the legs are substantially aligned, and diametrically opposed. The stalk or rod, carrying one or more staples in accordance with the present invention, is disposed in a tubular container or shell dimensioned for insertion in a biopsy channel of an endoscope or laparoscope, or other minimally invasive surgical device.

In a surgical stapling or fastening operation, a fastener is ejected from a mouth of the tubular shell and caused to span a tear, wound or opening in an internal tissue surface of a patient. The tear, wound or opening preferably extends at least partially perpendicularly to a line of travel or major axis of the stalk and the attached staple or surgical fastener. Ideally, a major axis of the hernia is within 45° of a perpendicular to a major axis of the stalk.

Subsequent to or simultaneously with the spanning of the opening (incision, tear, hernia) by the opened surgical staple, distal and proximal prongs or penetrating elements thereof are fixed in tissue on either side of the opening. The prongs may be fixed in the tissue in either order or simultaneously. Following a secure fixing of the prongs, the stalk is withdrawn from the eyelets or apertures of the staple, allowing the staple contract or close under spring forces. During this closure, the staple will tend to gather together and compress intervening tissue and close or keep closed an included portion of the hernia or tear. By affixing first one prong and subsequently the remaining prong, wound closure is aided by either insertion or withdrawal of the stalk, depending on whether the proximal or the distal prong is inserted into the tissues prior to the placement of a longitudinal force on the stalk. Compressive insertion forces may be place on the stalk by engaging unidirectional sliding or ratchet-type surfaces on a distal end of the stalk and inner surfaces of the eyelets of the staple, respectively. Tensile withdrawal forces may be achieved in the stalk by engagement of a retractable ball or detent on the distal end of the stalk with a distal eyelet of the staple. Following placement of the staple, the ball or detent is released by operator action on a proximal end of the stalk, transmitted by an internal actuator. Alternatively, a certain wound closure force may be achieved by friction between stalk and staple.

In accordance with an additional feature of the present invention, the stalk may be steerable or manipulable to facilitate a placement of the staple. In a first movement scheme, the stalk is steered by two elongate members in or along the stalk, the members being manipulated by an operator at a proximate end of the stalk to provide motion in two planes at a tip or distal end of the stalk. Alternatively, in a second movement scheme, a single degree of freedom coupled to an elongate member contained in the stalk, allowing movement of the tip in a single plane of motion, may be combined with a rotational degree of freedom of the stalk, allowing rotation of the plane of motion, in order to achieve flexibility of staple placement. In either movement scheme, motion of the stalk may be partially constrained by enclosure in a semi-rigid sheath or outer tube containing stalk and mounted staples or alternatively the stalk may be of bipartite construction including a relatively rigid body and relatively flexible distal tip or finger. Yet more complicated movement schemes may be devised by those skilled in the art for the distal tip of a stalk-like member of a laparoscopic or endoscopic instrument, limited only by space and strength of materials.

In a further extension of a surgical stapling operation, additional staples mounted on the stalk or manipulating element may be advanced to a distal tip thereof, and a sequence of steps for placement of a single surgical staple in accordance with the present invention may be repeated, placing additional staples to close a large hernia or tear in internal tissue of the patient.

The design of spring loaded staples and an associated surgical stapler assembly in accordance with the present invention, and a method for inserting these staples into tissue using the associated stapler assembly during a minimally invasive surgical procedure, will be apparent upon consideration of the detailed description in conjunction with the drawings.

BRIEF DESCRIPTION OF THE DRAWING

More particularly, FIG. 8 shows a staple partially protruding from a surgical stapler assembly in accordance with the present invention, penetrating a human body, while, FIG. 9 shows a surgical staple or fastener in accordance with the present invention spanning a hernia or tear in internal tissues of the human body, partially inserted in the tissues. FIG. 10 shows the staple of FIG. 9 fully inserted in the tissues, preparatory to withdrawal of a manipulating member or stalk. FIG. 11 shows the staple of FIG. 10 in a closed configuration, binding together sides of the hernia, subsequent to withdrawal of the manipulating member or stalk.

DETAILED DESCRIPTION OF THE INVENTION

Figure 1:
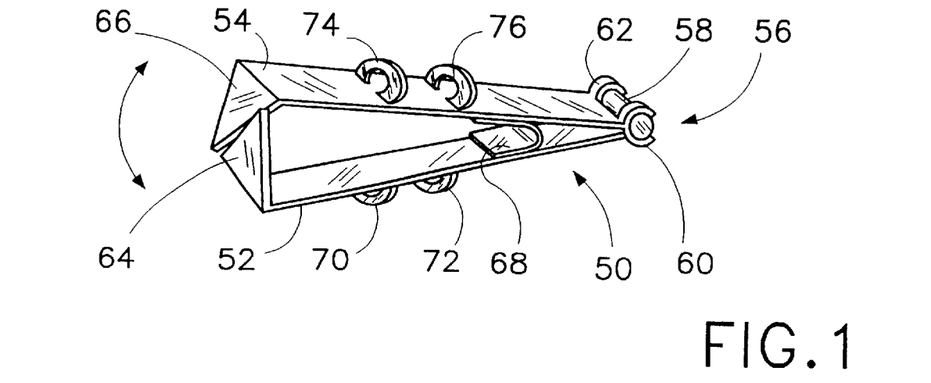
FIG. 1 is a perspective view of a surgical fastener in accordance with the present invention in a closed configuration.

A surgical fastener 50 as shown in FIG. 1 is useful to perform a surgical closure procedure in a minimally invasive operation such as an endoscopic operation. As used herein the term "endoscopic" embraces minimally invasive procedures wherein instruments are inserted in a patient through small openings, natural or incised. The term "flexible endoscopy" refers to procedures using flexible instruments, generally conducted via natural openings such as the mouth or the rectum. "Laporoscopic" and "laporoscopy" are used herein to denote use of rigid instruments generally inserted through rigid sleeves or cannulas traversing the skin. Surgical fastener 50 takes in the form of a staple or hinged clamp and comprises a first leg member 52 and second leg member 54 joined by a hinge 56. Hinge 56 comprises a pin element 58 affixed to one end of the first leg member, and a pair of slotted sleeves 60, 62 affixed to one end of the second leg member. Other combinations of interlocking elements affixed to the respective leg members may alternatively be utilized as a hinge. Free ends of leg members 52, 54 are provided with or formed into prongs or penetrating elements 64, 66 with points (not separately designated) directed inward in a sense determined by a spring biasing of staple 50. Spring biasing is provided by an elastomeric or leaf spring element 68 joining inside faces (not separately designated) of leg members 52, 54. Eyelets 70, 72 and 74, 76 are provided on outer faces (not separately designated) of leg members 52, 54 respectively, for receiving a bar or stalk (e.g., 148, FIGS. 6 and 7) which hold staple 50 in an open, essentially linear, configuration (FIG. 2), prior to affixment of the staple to human tissue in a stapling operation, as described hereafter.

Figure 2:
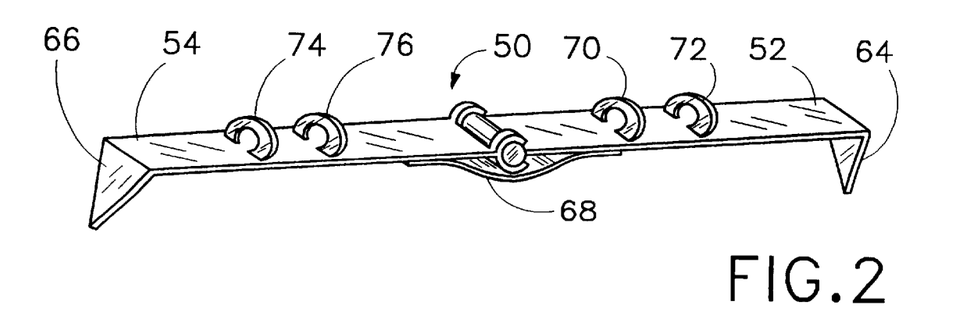
FIG. 2 is a perspective view of the surgical fastener or staple of FIG. 1 in an opened configuration.

An opened or prefiring configuration of staple 50 is shown in FIG. 2. In this illustration it may be readily seen that a bar or stalk (not illustrated) may be fed through eyelets 70, 72, 74, 76 to hold staple 50 in an opened and essentially linear configuration against the closing force exerted by spring element 68. When this restraining element is withdrawn from eyelets 70–76, staple 50 will tend to assume a closed configuration, grasping or piercing soft tissues between leg members 52, 54 with prongs or penetrating elements 64, 66.

Figure 3:
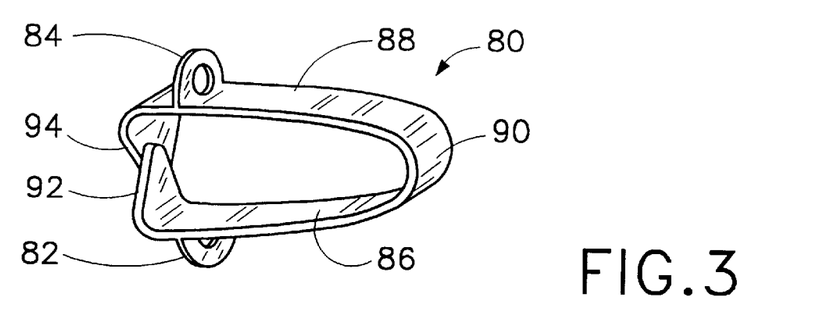
FIG. 3 is a perspective view of another surgical fastener or clip in accordance with the present invention in a closed configuration.

An alternative embodiment of a fastener comprising an integral or single piece staple 80 is illustrated in FIG. 3. Staple 80 is manufactured from a preform (not separately illustrated) made from spring steel or stainless steel or other suitable resilient material, completed by affixation of eyelets 82, 84, or alternatively may be molded in a single piece inclusive of eyelets in a suitable plastic resin formulation. A body element (not separately designated) of staple 80 comprises a first leg portion 86, a second leg portion 88 and a resilient intermediate or bight portion 90 joining the first leg portion and the second leg portion, and biasing the staple to a post-firing configuration wherein leg portions 86, 88 are adjacent and substantially parallel, as shown in FIG. 3. Staple 80 further includes tips or prongs 92, 94 terminating the body element and forming substantially0 degree angle with leg portions 86, 88.

Figure 4:
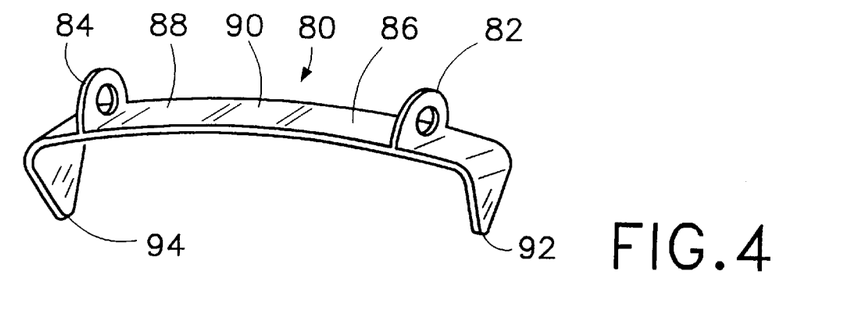
FIG. 4 is a perspective view of the fastener of FIG. 3 in an opened configuration.

Staple 80 is further illustrated in FIG. 4 in an open, or prefiring configuration, wherein leg portions 86, 88 are substantially collinear. In an open or prefiring configuration of staple 80, a locally rigid bar, dowel, stalk or other elongate member (not illustrated) may be inserted through eyelets 82, 84 to maintain the staple in an approximately linear conformation.

Figure 5:
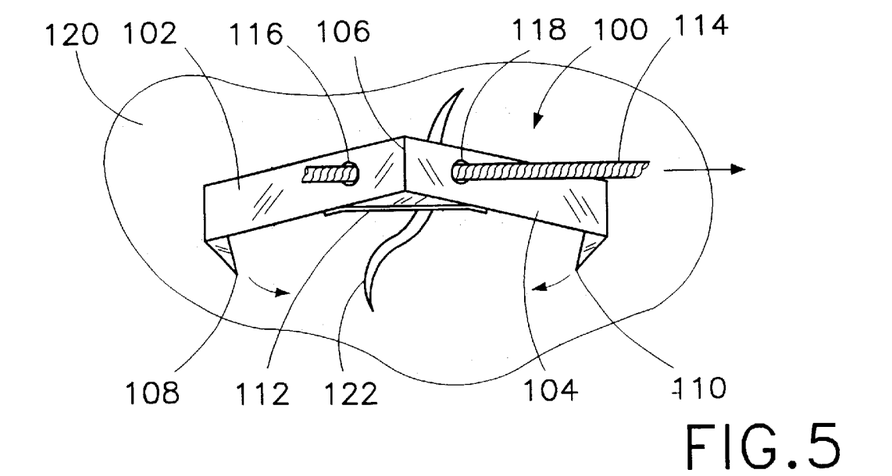
FIG. 5 is a perspective view of another fastener in accordance with the present invention, also showing a section of tissue and a manipulating member or stalk.

A further embodiment of a surgical fastener or staple 100 usable in a surgical fastener or staple assembly is illustrated in FIG. 5. Two substantially flat leaves or legs 102, 104 are pivotably joined at a fold line or hinge element 106. Prongs or teeth 108, 110 are affixed or formed at free ends of leaves 102, 104 and are angled towards an underside of the leaves.

An elastomeric band or spring element 112 is affixed to the underside of the leaves 102, 104, biasing the fastener or staple to a closed configuration (not illustrated) analogous to the configurations of fasteners 50, 80 in FIGS. 1 and 3 respectively.

A rigid or semi-rigid elongate member, taking the form of a rod or stalk 114 and passing through apertures 116, 118 in leaves 102, 104 respectively, holds fastener 100 in an opened configuration, as shown in FIG. 5. In a surgical fastening or stapling operation, fastener 100 is manipulated by means of inserted stalk 114 in a vicinity of soft tissue mass 120. Subsequent to an insertion of prongs 108 and 110 in tissue mass 120 on opposite sides of a tear or fissure 122, stalk 114 is withdrawn from fastener 100. Withdrawal of the stalk allows fastener 100 to relax towards a closed configuration under the action of spring element 112, tending to pierce and hold a portion of tissue mass 120 interposed between prongs 108, 110 and tending to close fissure or tear 122.

Figure 6:
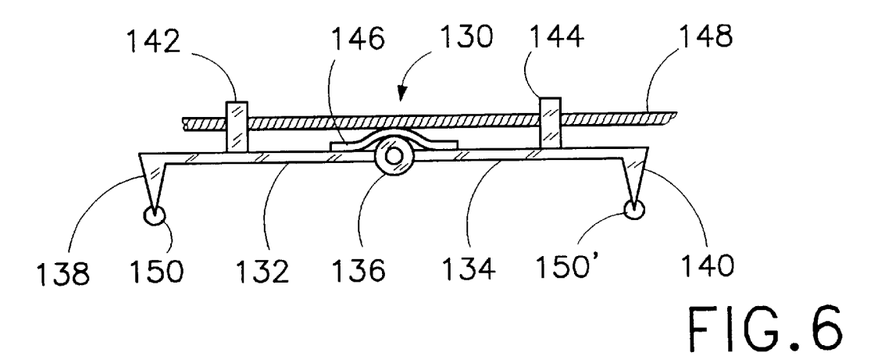
FIG. 6 is an elevational view of yet another surgical fastener in accordance with the present invention, also showing a manipulating member or stalk.

Yet a further embodiment of a surgical fastener or stapler utilizable in a surgical stapler assembly is illustrated in FIG. 6. Fastener 130 comprises two leg members 132, 134 pivotably connected by a hinge element 136. A leaf spring 146 is bonded to upper or outer sides (not separately designated) of legs 132, 134 and passes over hinge element 136. Analogously to previous embodiments, leaf spring 146 biases fastener 130 to a closed configuration (not illustrated) wherein a pair of teeth or prongs 138, 140 are proximate to one another and tend to grasp an interposed mass of soft tissue (not illustrated). Eyelets 142, 144 are affixed to leg members 132, 134 respectively, and are engageable by a semi-rigid stalk 148 to hold fastener 130 in an open position. Bio-inert tip protectors 150, 150' may optionally be affixed to tips (not separately designated) of teeth or prongs 138, 140, as will be explained more fully hereinbelow.

Fasteners 50, 80, 100 and 130 are essentially similar in concept and function, and have been included by way of illustration of the concepts of the present invention. Therefore nothing in description of employment of a particular embodiment in a surgical fastener assembly or surgical stapler is to be construed to limit the scope of the invention to employment of that embodiment. Rather the scope of the invention is to be construed to lie in the applications of the concepts thereof as illustrated by specific embodiments, and codified in the claims.

Figure 7:
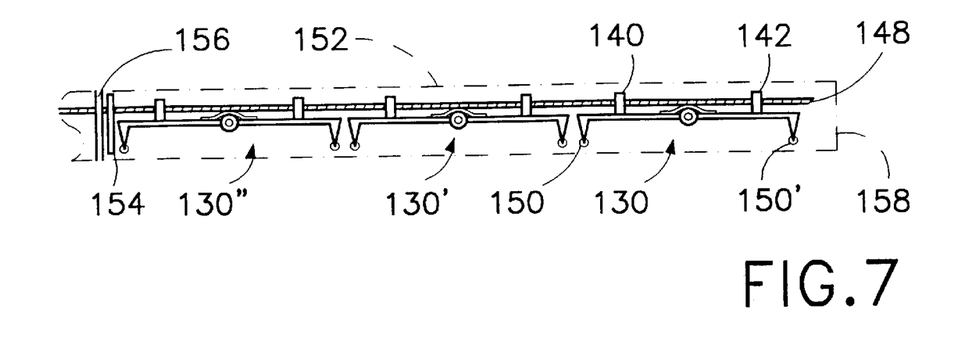
FIG. 7 is an elevational view of a surgical stapler assembly in accordance with the present invention, containing multiple units of the fastener or staple of FIG. 6 in a magazine.

A multiple surgical fastener assembly, or surgical stapler, is illustrated in FIG. 7. A multiplicity of surgical fasteners 130, 130', 130" are deployed in a cylindrical container 152 designed to sit in the biopsy channel of an endoscope or laparoscope.

Staples or fasteners 130, 130', 130" are mounted via eyelets 140, 142 on a stalk or semi-flexible elongate rod 148, which may be manufactured from a tightly coiled steel spring. In a stapling operation, stalk 148 is protruded from a mouth 158 of tube or cylindrical container 152 under the control of an operator (not illustrated) at a proximal end of the tube. A first stop element 154 is mounted via a friction fit on stalk 148 and causes staples 130, 130', 130" to move distally with the stalk. As staple 130 protrudes from tube 152, optional tip protectors 150, 150', if present, fall off tips 138, 140, and the staple is affixed to human tissue (not illustrated) in a manner which will be more fully described below.

Following affixation of staple 130 to internal tissues of a patient, stalk 148 is withdrawn into tube 152 until first stop element 154 contacts a second stop element 156 affixed to tube 148. The friction fit of first stop element 154 on stalk 148 is designed to present adequate resistance to move staples 130, 130', 130" outward under a distal movement of stalk 148, but allow element 154 to slide distally relative to stalk 148 upon a proximal movement of the stalk and engagement of first stop element 154 with tube-mounted second stop element 156. Stalk 148 is proximally shifted until staple 130' occupies a distal position on the stalk formerly occupied by staple 130. Stalk 148 is then distally moved to place staple 130' in a ready position immediately inside mouth 158 of tube 152, and subsequently protruded from mouth 158 in a repetition of the stapling operation described above. A complete sequence of steps in the stapling operation may be repeated until an exhaustion of staples in tube 152.

A surgical stapling operation is illustrated in a different aspect in FIGS. 8, 9, 10, and 11.

Figure 8:
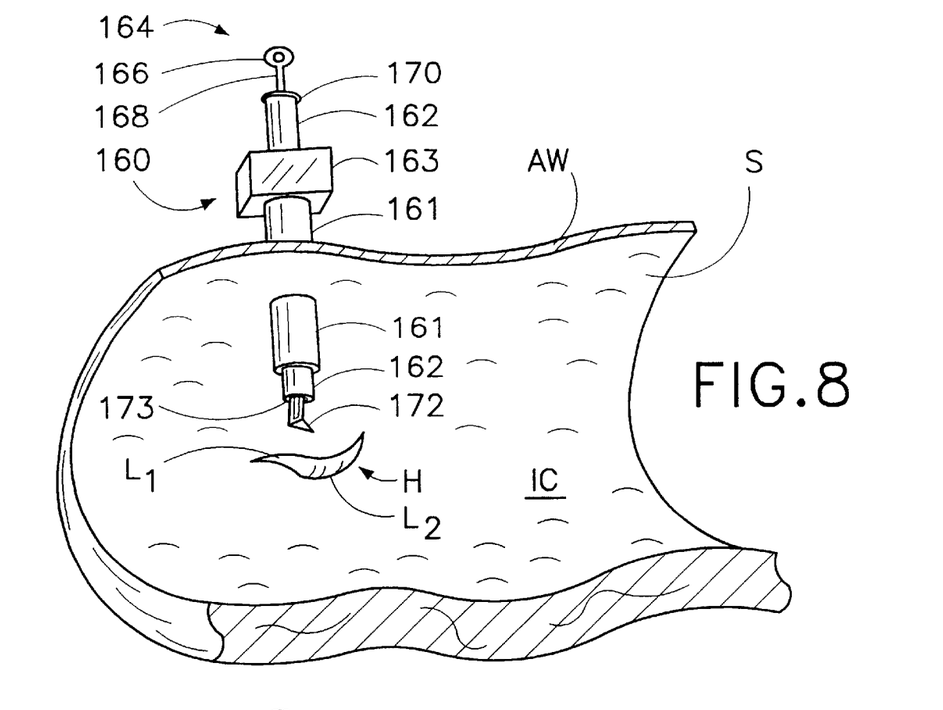
FIGS. 8 through 11 are schematic perspective views of a laparoscope containing a surgical stapler assembly in accordance with the present invention, and partially a cut-away of a human body, illustrating a sequence of steps in a laparoscopic stapling operation.

In FIG. 8, a trocar assembly 160 comprising trocar sleeve or cannula 161 and port member 163 is schematically shown traversing an abdominal wall AW of a patient. An access tube 162 of a laparoscopic stapling device 164 is shown inserted through sleeve or cannula 161 and projecting into an interior cavity IC of the patient. A handle or manipulating device 166 is attached to a semi-rigid stalk 168, which passes through a valved end cap 170 into tube 162. In FIG. 8, a staple 172 similar to staple 50 of FIGS. 1 and 2 is shown protruding from a mouth 173 of tube 162 preparatory to further steps in a surgical stapling operation to close a hernia or tear H defined by lips $L_1$, $L_2$, disrupting an interior surface S of patient P. Staple 172 is maintained in a open configuration, substantially identical to that shown in FIG. 2 for staple 50, by resistance or stalk 168 in opposition to a closing force of an integral spring member (not illustrated), similar to member 68 of FIGS. 1 and 2.

Figure 9:
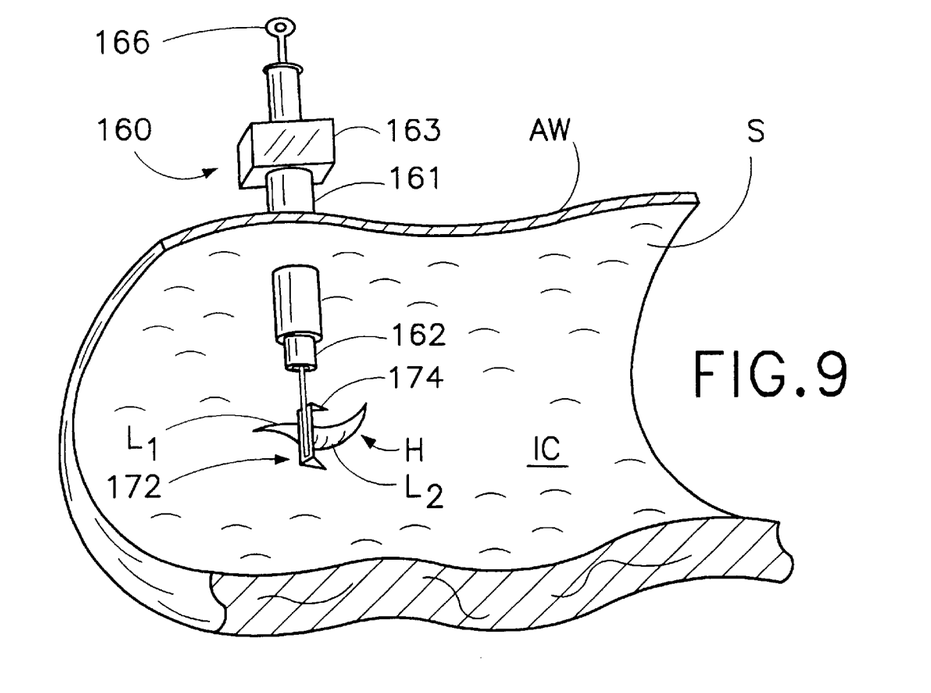
Figure 10:
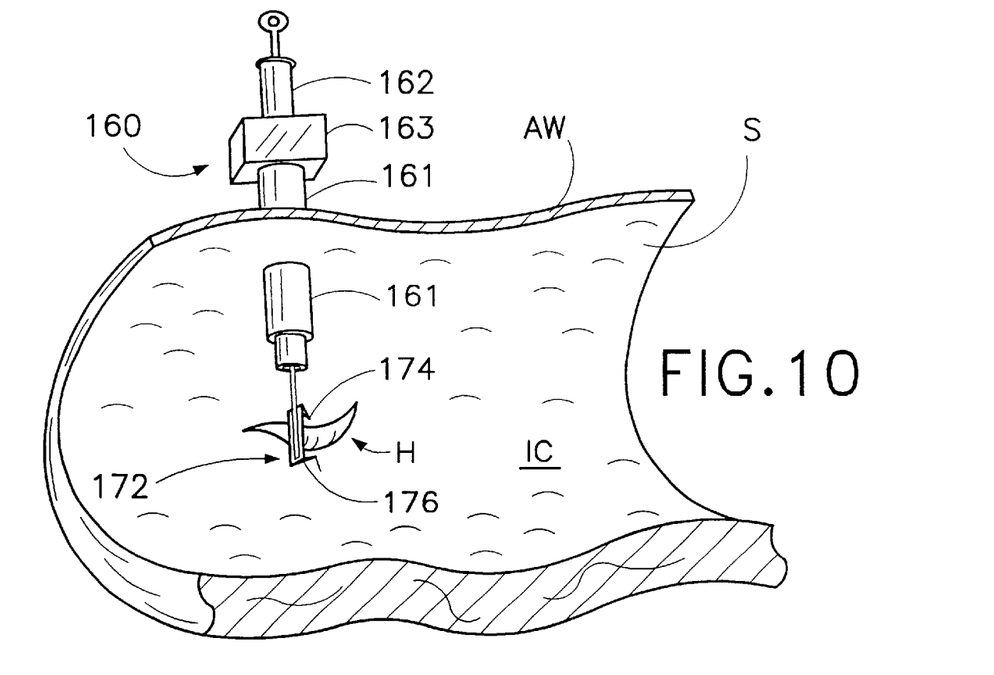
Figure 11:
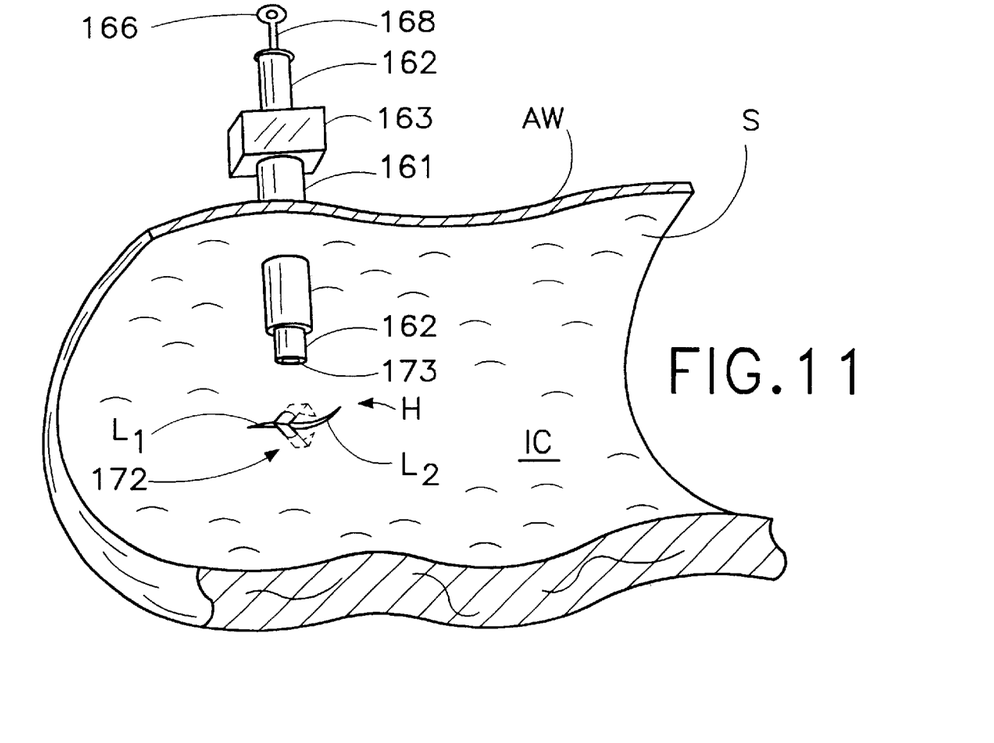

In FIG. 9, a further step in a surgical stapling operation is illustrated. Staple or fastener 172 has been advanced distally via manipulation of handle 166 to span hernia H, and a proximal point or prong 174 of staple 172 has been inserted in a cis-hernial region of interior surface S. Subsequent to insertion of proximal point 174, stalk 168 is further manipulated to insert a distal point or prong 176 of staple 172 in a trans-hernial region of surface S. In the course of this further manipulation, a compressive force is optionally applied to the stalk prior to insertion of the distal point, pushing a proximal edge or lip of the wound or hernia towards a distal lip or edge of the wound and assisting in closure of the wound prior to a release of the staple. Stalk 168 is subsequently proximally withdrawn through tube mouth 174 into tube 162, releasing staple 172. Subsequently, the staple contracts or closes under the action of the integral spring member, tending to further approximate or draw together lips $L_1$, $L_2$, and occlude hernia H. Alternatively, the distal point may be inserted first, and a tensile force optionally applied to the stalk prior to insertion of the proximal point, pulling the distal edge or lip of the wound towards the proximal edge of the wound and again assisting in closure of the wound prior to prior to release of the staple.

A repetition of the operation as described with reference to FIGS. 8–11 may then be undertaken as necessary. Multiple staples may be inserted from a magazine, as described in connection with FIG. 7. Alternatively, a simpler, single fastener, mode of operation of a surgical stapler assembly may be undertaken wherein stalk 168 is completely withdrawn from tube 162 subsequent to each placement of a single fastener, to enable a manual feeding of additional fasteners onto stalk 168. Other variations will occur to those skilled in the laparoscopic arts which do not deviate substantively from the spirit of the invention. Similar devices, techniques and assemblies may also clearly be applied in flexible endoscopy and in other minimally invasive surgical procedures and may find application in similar situations involving limited access and remote manipulation, for example, as an aid to repairs conducted in high radiation areas, or bio-hazardous or sterile environments.

Figure 12:
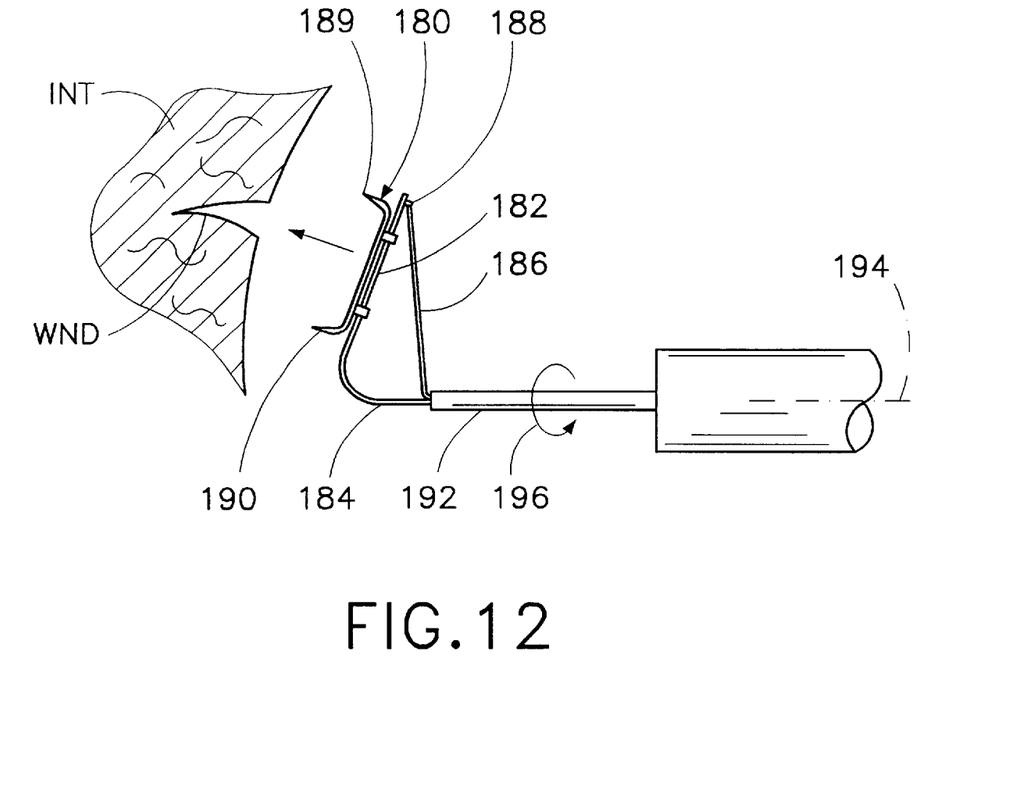
FIG. 12 is a schematic side elevational view of another embodiment of a surgical staple deployment assembly in accordance with the present invention.

As illustrated in FIG. 12, a surgical fastener or staple 180 is removably mounted in an open pre-firing configuration to a distal end portion 182 of a stalk or rod 184. An elongate tensile element 186 exemplarily in the form of a wire is fastened at 188 to a distal tip of stalk or rod 184 for purposes of bending distal end portion 182 relative to a main body (not designated) of stalk or rod 184, thereby enabling an operator to optimally orient staple 180 prior to an insertion of distal and proximal staple prongs 189 and 190 into internal tissues INT of a patient on opposite sides of a wound or other opening WND. Wire 186 extends from tip 188 to an auxiliary sheath 192 enclosing a portion of stalk or rod 184. Pulling a proximal end of wire 186 introduces tension into the wire and causes a flexing of stalk or rod 184 at a point proximal to distal end portion 182 in opposition to an internal spring force tending to return stalk or rod 184 to a linear configuration. The angle of distal end portion 182 relative to the main body of stalk or rod 184 may be controlled by varying the tension placed on wire 186. In addition, stalk or rod 184 is rotatable about its longitudinal axis 194, as indicated by an arrow 196, whereby staple 180 may be applied to tissues having a wide range of locations and orientations. Other equivalent techniques for steering stalk or rod 184 will be apparent to those skilled in the art. For instance, stalk or rod 184 may be steered by two elongate tensile members (not illustrated) in or along the stalk, the members being manipulated by an operator at a proximate end of the stalk to provide motion in two planes at a tip or distal end of the stalk.

Although the invention has been described in terms of particular embodiments and applications, one of ordinary skill in the art, in light of this teaching, can generate additional embodiments and modifications without departing from the spirit of or exceeding the scope of the claimed invention. In placement of a surgical staple utilizing methods and assemblies of the present invention, development of compressive or tensile forces in the stalk in balance to a force of the staple exerted on human tissue may be aided by the use of detents or ratchet-like configurations, and the manipulation of the staple may be aided by steering mechanisms discussed herein above, and which will be apparent to those skilled in the relevant mechanical and surgical arts (none shown).

Accordingly, it is to be understood that the drawings and descriptions herein are proffered by way of example to facilitate comprehension of the invention and should not be construed to limit the scope thereof.

What is claimed is:

1. A surgical stapling device comprising:
   a staple including:
   (i) a first leg;
   (ii) a second leg pivotably joined to said first leg; and
   (iii) a spring element connected to said first leg and said second leg for biasing said staple in a closed post-firing configuration wherein said first leg and said second leg are adjacent and substantially parallel; and
   an assembly operatively coupled to said first leg and said second leg for releasably maintaining said staple in an open prefiring configuration wherein said first leg and said second leg are substantially collinear, so that upon release the first leg and the second leg are forcibly drawn together by said spring element into said post-firing configuration, said assembly having a longitudinal axis, said staple in said open prefiring configuration being oriented parallel to said axis.

2. The surgical staple assembly set forth in claim 1 wherein said open prefiring configuration of said staple has a pair of spaced free ends, said staple being disposed in said assembly for maintaining so that one of said spaced free ends is ejected from said assembly prior to another one of said spaced free ends during a staple firing operation.

3. The surgical staple assembly set forth in claim 2 wherein said assembly for maintaining includes a tubular member having an ejection port or a mouth at one end, said staple being disposed in said open prefiring configuration in said tubular member so that one of said spaced free ends is disposed closer to said ejection port or mouth than another one of said spaced free ends.

4. The surgical staple assembly set forth in claim 1 wherein said assembly includes projections on said first leg and said second leg and means coupled to said projections holding said first leg and said second leg in said open prefiring configuration.

5. The surgical staple assembly set forth in claim 1, further comprising penetrating elements joined to said first leg and said second leg for piercing organic tissues to facilitating a constriction of the organic tissues by said staple in said closed post-firing configuration, said penetrating elements projecting substantially orthogonally with respect to said axis.

6. The surgical staple assembly set forth in claim 1 wherein said spring element comprises a resilient intermediate portion joining said first leg and said second leg and biasing said staple to hold said first leg and said second leg adjacent and substantially parallel in said post-firing configuration.

7. The surgical staple assembly set forth in claim 6 wherein said open prefiring configuration of said staple has a pair of spaced free ends, said staple being disposed in said assembly for maintaining so that one of said spaced free ends is ejected from said assembly prior to another one of said spaced free ends during a staple firing operation.

8. The surgical staple assembly set forth in claim 7 wherein said assembly for maintaining includes a tubular member having an ejection port or a mouth at one end, said staple being disposed in said open prefiring configuration in said tubular member so that one of said spaced free ends disposed closer to said ejection port or mouth than another one of said spaced free ends.

9. The surgical staple assembly set forth in claim 6, wherein said assembly includes projections on said first leg and said second leg and means coupled to said projections for holding said first leg portion and said second leg in said open prefiring configuration.

10. The surgical staple assembly set forth in claim 1, further comprising a pivoting structure or hinge connecting said first leg and said second leg to one another, said spring being a separate element attached to said first leg and said second leg.

11. A surgical device utilizable in an endoscopic stapling operation, comprising:
a tubular casing adapted for insertion in an endoscopic instrument, said tubular casing having an ejection port or mouth at one end;
a stalk member slidably disposable inside said tubular casing;
an actuator operatively connected to said stalk member for longitudinally shifting said stalk member with respect to said tubular casing; and
a surgical staple disposed inside said tubular casing, said staple having a pair of legs pivotably connected to one another at a joint, said legs being provided with a spring element elastically biasing the staple to a closed post-firing configuration, said legs also being provided with at least two openings traversed by said stalk member to hold the staple in an open prefiring configuration having one end disposed substantially closer than an opposite end to said ejection port or mouth.

12. The surgical device set forth in claim 11 wherein said staple is disposed inside said tubular casing upon mounting of the staple on said stalk member.

13. The surgical device set forth in claim 11 wherein a multiplicity of staples are disposed within said tubular casing and mounted to said stalk member, each of said staples having a linear opened configuration having a pair of spaced free ends, said staples being oriented end to end in said tubular casing.

14. The surgical device set forth in claim 11 wherein said spring element comprises a resilient bight portion joining said legs to one another to hold said legs adjacent and substantially parallel in said post-firing configuration, said legs being provided with at least two openings traversed by said stalk member to hold the staple in a open prefiring configuration.

15. The surgical device set forth in claim 14 wherein said staple is disposed inside said tubular casing upon mounting of the staple on said stalk member.

16. The surgical device set forth in claim 14 wherein a multiplicity of staples are disposed within said tubular casing and mounted on said stalk member, each of said staples having a linear opened configuration having a pair of spaced free ends, said staples being oriented end to end in said tubular casing.

17. A surgical fastening method comprising:
providing an access tube, an elongate stalk or rod, and a spring biased surgical fastener having a first prong and a second prong, said surgical fastener being mounted in an open configuration on a distal end portion of said stalk or rod, said distal end portion of said stalk or rod and said surgical fastener being disposed in said access tube;
inserting said access tube into a patient so that said access tube extends from an external to an internal region of the patient;
after insertion of said access tube, ejecting said surgical fastener and said distal end portion of said stalk or rod from said access tube into the patient so that one of said first prong and said second prong exits said access tube prior to the other of said first prong and said second prong;
manipulating said stalk or rod to place said first prong into a first tissue surface;
manipulating said stalk to place said second prong into a second tissue surface; and
following placement of said first prong and said second prong, withdrawing said stalk to release said fastener and enable a compression by the spring bias of said surgical fastener of tissue interposed between said first prong and said second prong.

18. The method described in claim 17 wherein said surgical fastener has a first leg and a second leg, said stalk or rod being inserted through a first aperture in said first leg and through a second aperture in said second leg.

19. The method described in claim 17 wherein said surgical fastener has a first leg and a second leg, said stalk or rod being inserted through a first eyelet affixed to said first leg and through a second eyelet affixed to said second leg.

20. The method described in claim 17 wherein the providing of said access tube, said stalk or rod and said fastener includes inserting said stalk or rod and said fastener into said access tube.

21. The method described in claim 17 wherein said tissue interposed between said first prong and said second prong includes a wound, said first tissue surface being located on one side of said wound, said second tissue surface being disposed on an opposite side of said wound.

22. The method described in claim 21, further comprising applying a longitudinal force to said stalk or rod subsequent to placement of said first prong and prior to placement of said second prong, tending to close said wound prior to placement of said second prong.

23. The method described in claim 22 wherein said first prong is a proximal prong and said longitudinal force is a compressive force.

24. The method described in claim 22 wherein said first prong is a distal prong and said longitudinal force is a tensile force.

* * * * *